United States Patent
Ng et al.

[11] Patent Number: 5,869,452
[45] Date of Patent: Feb. 9, 1999

[54] TREATMENT OF OBESITY

[75] Inventors: Frank Man-Woon Ng, Kew; Siria Helen-Anna Natera, Mount Waverly; Woei-Jia Jiang, Clayton, all of Australia

[73] Assignee: Monash University, Clayton, Australia

[21] Appl. No.: 340,389

[22] Filed: Nov. 15, 1994

[51] Int. Cl.⁶ .............................. A61K 38/03; C07K 7/00
[52] U.S. Cl. ........................ 514/14; 514/12; 514/13; 530/324; 530/326
[58] Field of Search .................. 530/324, 326; 514/14, 12, 13

[56] References Cited

U.S. PATENT DOCUMENTS

| | | | |
|---|---|---|---|
| 4,863,901 | 9/1989 | Wilmore | 514/12 |
| 4,871,835 | 10/1989 | Aviv et al. | 530/399 |
| 5,597,797 | 1/1997 | Clark | 514/12 |

OTHER PUBLICATIONS

"Antilipogenic Action Of Synthetic C–Terminal Sequence 177–191 Of Human Growth Hormone," *Biochemistry and Molecular Biology International* vol. 30:1 187–96 (May 1993).

Jean Marx, Science, vol. 266, Dec. 2, 1994.
Rink, Timthoy, Nature, vol. 372 1 406–407, (Dec. 1, 1994), pp. 406–407.
Natera, et al., Biochemistry and Molecular Biology International, vol. 33, No. 5, Aug., 1994.
Wijaya et al., Biochemistry and Molecular Biology International, vol. 31, No. 3, Nov. 1993.
Campbell et al., Proc. Soc. Exper. Biol. Med. vol. 193 No 4 (Apr./1990) pp. 269–273.
Ma et al., Biochem. et Biophys. Actg 716 (1982) 400–409.
Nishikawa et al., Prot. Engin. vol. 3 No. 1 pp. 49–53 (1989).
Newman et al., Biochim. et Biophys. Acta 544 (1978) 234–244.
Remington's Pharmaceutical Sciences, 18th ed. 1990 pp. 1633–1636, 1676–1679.

*Primary Examiner*—Cecilia J. Tsang
*Assistant Examiner*—Bennett Celsa
*Attorney, Agent, or Firm*—Foley & Lardner

[57] ABSTRACT

A method for the treatment of obesity in an animal such as a human, comprises administering to the animal an effective amount of a peptide which comprises the carboxyl-terminal sequence of a growth hormone, particularly the carboxyl-terminal sequence of human growth hormone containing amine acid residues 177–191. A pharmaceutical composition for use in the treatment of obesity is also disclosed.

5 Claims, 2 Drawing Sheets

TREATMENT OF OBESITY

FIELD OF THE INVENTION

This invention relates to the treatment of obesity in animals. In particular, the invention relates to the treatment of obesity in humans, although it is to be understood that the present invention also extends to the treatment of obesity in non-human mammals, for example, for the improvement of meat qualities in farm animals used in food production.

BACKGROUND OF THE INVENTION

The critical role of human growth hormone (hGH) in postnatal growth in humans is well recognised. Less obvious is the impact of this hormone on the regulation of lipid and carbohydrate metabolism, due to lack of detailed molecular studies.

It is well documented that the predominant form of hGH is a globular protein with a molecular weight of 22,000 daltons (22-KD) and consists of 191 amino acid residues in a single-chain, folded by 2 disulphide bonds with a small loop at the carboxyl terminus between residues 182 and 189. Recent crystallographic studies also show that the hGH molecule contains four anti-parallel α-helices which are arranged in a left-twisted, tightly-packed helical bundle[1]. The concept that there are discrete functional domains within the hGH molecule responsible for specific metabolic actions of the hormone is generally accepted. The amino-terminus has been identified as the functional domain responsible for the insulin-like actions of the hGH molecule[2,3].

Recombinant DNA technology opens the way to the large-scale commercial production of human growth hormone, and the recombinant hGH appears to have equivalent biological efficacies and pharmacokinetic properties[4,5]. Current supply of this multiple-functional hormone no longer restricts the types and numbers of experimental therapies in humans and animals. The use of hGH for treatment of short stature in children and adults is well-established[6]. Therapeutic effects of hGH in female infertility have also been reported[7,8]. Treatment of human obesity with hGH has been advocated because of its remarkable effects on body composition with lipid metabolism[9]. However, the clinical applications of the intact hormone encounter a variety of problems. Evidence suggests that this multiple-functional hormone often simultaneously exerts in vivo, by various bioactive domains within the molecules, some adverse effects[10].

Regulation of lipid metabolism by GH was first described in 1959 by Raben & Hollenberg[11]. The acute increase of plasma free fatty acids after GH administration was the major evidence for this metabolic function of the hormone. The regulatory role of the hormone in lipid metabolism was subsequently supported by the body composition studies of GH-deficient and GH-treated humans[12,13] and pigs[14,15]. The findings of Gertner suggest that hGH is linked to adipose tissue distribution through a series of interactions known as the "GH-fat cycle"[16]. However, the molecular events transpiring to these biochemical and physiological changes remained largely unknown. The metabolic effects of GH on adipose and other tissues in vivo are variable and complex, apparently consisting of at least two components, an early insulin-like effect followed by a later more profound anti-insulin effect[17]. The results of the latter effect may include both a stimulation of lipolysis and an inhibition of lipogenesis. The anti-lipogenic effect of hGH has been substantiated with the demonstrations of the decrease of the expression of glucose transporter GLUT 4 in adipocytes[18], the inhibition of the activity of acetyl-CoA carboxylase in adipose tissues[19,20] and the reduction of glucose incorporation into lipid in both isolated cells and tissues[21,22].

In view of the multiple-functional effects of intact hGH and the problems encountered in clinical applications of the intact hormone, work leading to the resent invention has been directed to investigating whether hGH derivatives could be synthesised that retain the desired bioactivities and lack the unwanted side effects. In this work, structure-function studies of hGH have been carried out to elucidate the molecular mechanism of the metabolic actions of this multiple-functional hormone.

The structure-function studies of hGH with synthetic hormonal fragments have revealed that the carboxyl terminus of the hGH molecule appears to be the functional domain of the hormone for the regulation of lipid metabolism[20,23,24,25] and it has now been shown that a synthetic peptide having a sequence based in the carboxyl terminal region reduces body weight gain and adipose tissue mass in a laboratory obese animal model.

SUMMARY OF THE INVENTION

The present invention concerns a method for treating obesity comprising administering an effective amount of a peptide which comprises the carboxyl-terminal sequence of a growth hormone. The treatment may be administered to any animal, including humans. The peptide may comprise the carboxyl-terminal sequence of human growth hormone or the growth hormone of a non-human mammalian specie. In one embodiment of the invention, the peptide comprises the carboxyl-terminal sequence of human growth hormone containing amino acid residues 177–191. In other embodiments of the invention, the peptide comprises a homologue, analogue, mutant, variant or derivative obtained by insertion, deletion or substitution of amino acids in, or chemical modification of, the native carboxyl-terminal sequence of human growth hormone or the growth hormone of a non-human mammalian species.

The present invention also concerns a pharmaceutical composition for use in the treatment of obesity comprising an effective amount of a peptide which comprises the carboxyl-terminal sequence of a growth hormone and one or more pharmaceutically acceptable carriers and/or diluents. The peptide may comprise the carboxy-terminal sequence of human grouth hormone or the growth hormone of a non-human mammalian specie. In one embodiment of the invention, the peptide comprises the carboxyl-terminal sequence of human growth hormone containig amino acid residues 177–191. In other embodiments of the invention, the pdptide comprises a homologue, analogue, mutant, variant or derivative obtained by insertion, deletion or substitution of amino acids in, or chemical modification of, the matice carboxyl-terminal sequence of human growth hormone or the growth hormone of a non-human mammalian species.

DESCRIPTION OF THE PREFERRED EMBODIMENTS

According to one aspect of the present invention, there is provided a method for the treatment of obesity in an animal, which comprises administering to the animal an effective amount of a peptide which comprises the carboxyl-terminal sequence of a growth hormone.

As used throughout this specification, the term "obesity" is used to include both excess body weight and excess adipose tissue mass in the animal, and correspondingly the references to treatment of obesity include both reduction of body weight gain and reduction of adipose tissue mass of the obese animal.

Preferably, the animal is a human although the invention also extends to the treatment of non-human mammals. Preferably also, the peptide comprises the carboxyl-terminal sequence of human growth hormone containing amino acid residues 177–191 (hereinafter referred to as hGH 177–191). Alternatively, the peptide may comprise the carboxyl-terminal sequence of the growth hormone of other non-human mammalian species, such as bovine, porcine, ovine or equine growth hormone, corresponding to the hGH 177–191 peptide.

It will, of course, be appreciated that the present invention extends to the use of peptides having longer amino acid sequences than the particular sequence 177–191 of growth hormone, for example the sequence 172–191 of human growth hormone (SEQ ID NO:2) or the corresponding sequence of growth hormone of other non-human mammalian species, however the present invention does not extend to the use of intact full-length human growth hormone or growth hormone of other animal species. The present invention also extends to the use of peptides which are homologues, analogues, mutants, variants or derivatives of the native carboxyl-terminal sequences of human growth hormone or growth hormone of other animal species, and which are derived from natural or synthetic (including recombinant) sources, provided always that the resulting peptide retains the biological activity of the native carboxyl-terminal sequence described herein, namely the ability to reduce body weight gain and adipose tissue mass in an obese animal.

These homologues, analogues, mutants, variants or derivatives may be derived by insertion, deletion or substitution of amino acids in, or chemical modification of, the native carboxyl-terminal sequence. Amino acid insertional derivatives include amino and/or carboxylic terminal fusions as well as intra-sequence insertions of single or multiple amino acids. Insertional amino acid sequence variants are those in which one or more amino acid residues are introduced into a predetermined site in the protein although random insertion is also possible with suitable screening of the resulting product. Deletional variants are characterised by the removal of one or more amino acids from the sequence. Substitutional amino acid variants are those in which at least one amino acid residue in the sequence has been replaced by another of the twenty primary protein amino acids, or by a non-protein amino acid. Chemical modifications of the native carboxyl-terminal sequence include the acetylation of the amino-terminus and/or amidation of the carboxyl-terminus and/or side chain cyclisation of the native carboxyl-terminal sequence.

The term "effective amount" as used herein means an amount of the peptide sufficient to attain the desired effect in the treatment of obesity in the animal, but not so large an amount as to cause serious side effects or adverse reactions.

In another aspect, the present invention provides the use of an effective amount of a peptide which comprises the carboxyl-terminal sequence of a growth hormone as described above in the treatment of obesity in an animal or in the manufacture of a pharmaceutical composition for the treatment of obesity in an animal.

In yet another aspect, the present invention provides a pharmaceutical composition for use in the treatment of obesity in an animal, comprising an effective amount of a peptide which comprises the carboxyl-terminal sequence of a growth hormone as described above, together with one or more pharmaceutically acceptable carriers and/or diluents.

The peptide which is the active ingredient of the pharmaceutical composition of this aspect of the invention exhibits advantageous therapeutic activity in the treatment of obesity in an animal when administered in an amount appropriate to the particular case. For example, from about 0.5 $\mu$g to about 20 mg per kilogram of body weight per day may be administered. Dosage regimens may be adjusted to provide the optimum prophylactic or therapeutic response. For example, one or more divided doses may be administered daily, weekly, monthly or in other suitable time intervals or the dose may be proportionally reduced as indicated by the exigencies of the clinical situation.

The active ingredient may be administered in any convenient manner such as by the oral, parenteral (including intraperitoneal, intravenous, subcutaneous, intramuscular and intramedullary injection), intranasal, intradermal or suppository routes or by implanting (eg using slow release molecules). For ease of administration, oral administration is preferred, however parenteral administration is also quite convenient. Depending on the route of administration, the active ingredient may be required to be coated in a material that protects said ingredient from the action of enzymes, acids and other natural conditions which may inactivate the said ingredient. For example, low lipophilicity of the ingredient may allow it to be destroyed in the gastrointestinal tract by enzymes capable of cleaving peptide bonds and in the stomach by acid hydrolysis. In order to administer the composition by other than parenteral administration, the active ingredient may be coated by, or administered with, a material to prevent its inactivation.

The active ingredient may also be administered in dispersions prepared in glycerol, liquid polyethylene glycols, and/or mixtures thereof and in oils. Under ordinary conditions of storage and use, these preparations will usually contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thiomorosal, and the like. In many cases, it will be preferable to include isotonic agents, for example, sugars or sodium chloride. Prolonged absorption of the injectable compositions can be brought about by, for example, the use in the compositions of agents delaying absorption.

Sterile injectable solutions are prepared by incorporating the active ingredient in the required amount in the appropriate solvent with various of the other ingredients enumerated above, as required, followed by filtered sterilisation. Generally, dispersions are prepared by incorporating the sterilised active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active ingredient is suitably protected as described above, the composition may be orally administered, for example, with an inert diluent or with an assimilable edible carrier, or it may be enclosed in hard or soft shell gelatin capsule, or it may be compressed into tablets, or it may be incorporated directly with the food of the diet. For oral administration, the active ingredient may be incorporated with excipients and used in the form of ingestable tablets, buccal tablets, troches, capsules, elixirs, suspensions, syrups, wafers, and the like. Such compositions and preparations should contain at least 0.01% by weight and more preferably at least 0.1–1% by weight of active ingredient. The percentage of the compositions and preparations may, of course, be varied and may conveniently be between about 5 to about 80% of the weight of the unit. The amount of active ingredient in the pharmaceutical compositions is such that a suitable dosage will be obtained. Preferred compositions or preparations according to the present invention may, for example, be prepared so that an oral dosage unit form contains between about 0.5 μg and 200 mg and more preferably 10 μg and 20 mg of active ingredient.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active ingredient may be incorporated into sustained-release preparations and formulations.

As used herein, pharmaceutically acceptable carriers and diluents include any and all solvents, dispersion media, aqueous solutions, coatings, antibacterial and antifungal agents, isotonic and absorption delaying agents, and the like. The use of such media and agents for pharmaceutically active substances is well known in the art, and it is described, by way of example, in *Remington's Pharmaceutical Sciences*, 18th Edition, Mack Publishing Company, Pennsylvania, U.S.A. Except insofar as any conventional media or agent is incompatible with the active ingredient, use thereof in the pharmaceutical compositions of the present invention is contemplated. Supplementary active ingredients can also be incorporated into the compositions.

It is especially advantageous to formulate compositions in dosage unit form for ease of administration and uniformity of dosage. Dosage unit form as used herein refers to physically discrete units suited as unitary dosages for the human subjects to be treated; each unit containing a predetermined quantity of active ingredient calculated to produce the desired therapeutic effect in association with the required pharmaceutical carrier and/or diluent. The specifications for the novel dosage unit forms of the invention are dictated by and directly dependent on (a) the unique characteristics of the active ingredient and the particular therapeutic effect to be achieved, and (b) the limitations inherent in the art of compounding such an active ingredient for the treatment of obesity.

Throughout this specification and claims which follow, unless the context requires otherwise, the word "comprise", or variations such as "comprises" or "comprising", will be understood to imply the inclusion of a stated integer or group of integers but not the exclusion of any other integer or group of integers.

Further details of the present invention will be apparent from the following Example and the accompanying drawings which are included by way of illustration, not by way of limitation, of this invention.

EXAMPLE

MATERIALS AND METHODS

Animals and treatments

Figure 1A:
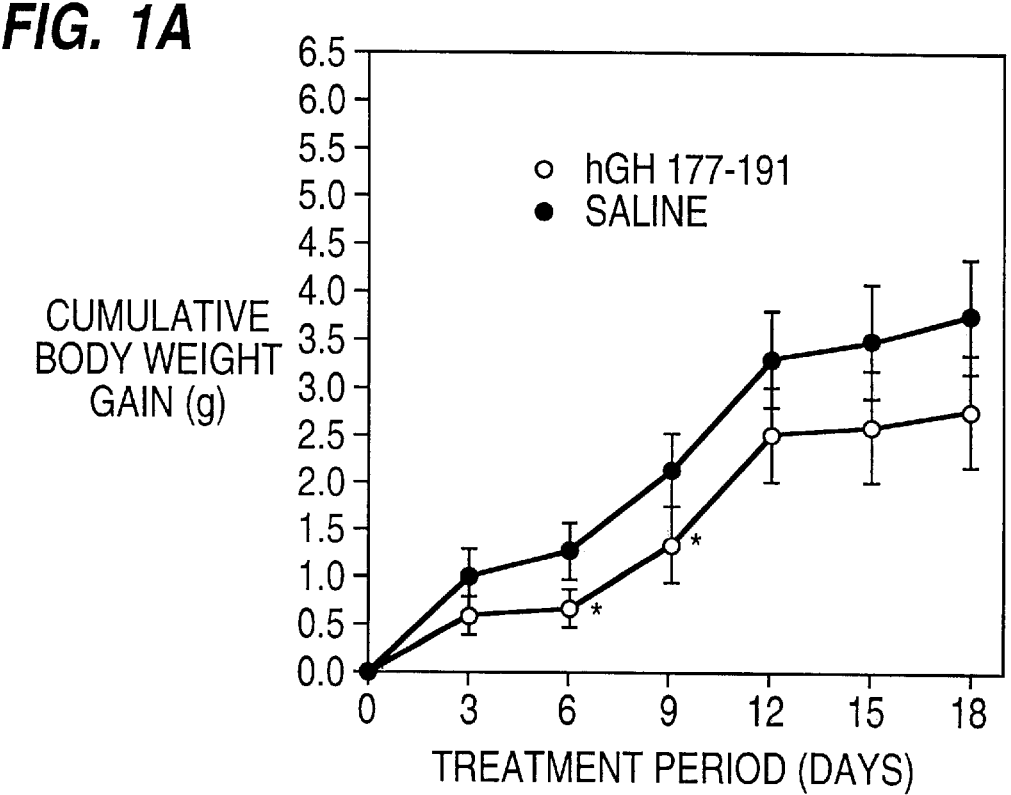
FIG. 1 shows the effect of hGH 177–191 peptide on cumulative weight gains in male (panel A) and female (panel B) C57BL/6J (ob/ob) mice during an 18-day treatment period. Animals were given a daily intraperitoneal injection of 0.1 ml of either saline (●, ▼) or synthetic hGH 177–91 peptide (200 μg/kg body weight) (o, ▽). Body weight changes were determined at 3-day intervals and each point represents the mean±SEM of 6 animals. The differences between the saline control and the hGH 177–191 treated groups were statistically analysed. *$P<0.05$ and **$p<0.025$ compared with corresponding controls.

Twelve male and twelve female C57BL/6J (ob/ob) mice aged 12–13 weeks were used in this study. The animals of the same sex were randomly divided into two groups, housed 6 per cage and maintained on a normal 12-hr light/dark cycle at a constant room temperature of 25° C. in the animal house of the Biochemistry Department, Monash University, Clayton, Australia. Animals were fed ad libitum on pre-determined quantity of mouse pellets (Clark King, Melbourne, Australia) and allowed free access to water at all times. The mice were given a daily intraperitoneal (i.p.) injection of 0.1 ml of either the hGH 177–191 peptide (200 µg/kg body weight) or equivalent volume of physiological saline (0.9% sodium chloride) for 18 days. The i.p. injection was administered with a 30G×½ "(0.31×13 mm) needle on a 1-ml disposable tuberculin syringe, and the site of injection as the lower left quadrant of the abdomen of the animals.

Peptide synthesis hGH 177–191,

Leu—Arg—Ile—Val—Gln—Cys—Arg—Ser—Val—Glu—Gly—Ser—Cys—Gly—Phe(SEQ ID NO: 1), was prepared by manual solid-phase synthesis of Fmoc-strategy using DIC/HOBt activation. The coupling reactions were monitored by using the ninhydrin method[26]. Acetamidomethyl(Acm) group was used for the side-chain protective group of two Cys residues. After completion, the peptide was cleaved from the resin and side-chain protective groups, except Acm, were removed by using Reagent K[27]. Removal of two Acm groups and simultaneous formation of the disulfide bond between Cys182 and Cys189 of hGH 177–191 were performed using the silyl-sulfoxide method[28]. Alternatively, other methods for formation of direct disulfide bonds may be used. After purification on RP-HPLC, the oxidised hGH 177–191 peptide was characterised with Waters Pico Tag (PITC) system for amino acid analysis [Arg: 1.92 (2), Cys: not determined (2), Glu/Gln: 2.00 (2), Gly: 2.27 (2), Ile: 0.84 (1), Leu: 1.19 (1), Phe: 1.10 (1), Ser: 1.54 (2), Val: 1.84 (2)] and with fast atom bombardment-mass spectrometer (FAB-Mass) for molecular weight determination, $[M+H]^+ +1652.0$ (experimental) for 1651.9 (calculated).

Cumulative weight gain and food consumption

Cumulative weight gain and food consumption were determined at 3-day intervals by the measurements of body weight and uneaten food remaining in the cages. The animals were placed in a covered chamber to minimise movement during the weighing procedure. The food consumption data were obtained by subtracting the amount of uneaten food remaining in the cages from the original provision.

Assays for plasma triglyceride and total cholesterol

The animals were anaesthetised with sodium pentobarbitone (80 mg/kg body weight) 12 hr after the last dose of hGH 177–191. Blood samples were collected from the tail vein of anaesthetised animals 45 mins after the administration of anaesthetic. After being centrifuged at 2000×g for 5 minutes, plasma was removed from the samples and used for metabolite assays. Triglyceride and total cholesterol in plasma were measured by enzyme-spectrophotometric methods. The reagents are based on either a modified glycerol phosphate oxidase (GPO)-Trinder's type colour reaction[29] or a cholesterol oxidase-4-aminoantipyrine method[30]. All assays were performed with the CentrifiChem System 400 (Union Carbide) containing an automated pipetter, a centrifugal analyser and a recording spectrophotometer. Seronorm Lipid (Nycomed Pharma Co., Oslo, Norway) was used as the calibrator.

Determination of adipose tissue weight

The procedure for the isolation and measurement of intact epididymal fat pads was established in previous studies of epididymal growth of GH-deficient (lit/lit) mice. In the present study, white adipose tissues, either whole epididymal or parametrical fat pads, were excised with the identical techniques as previously described[22] from the mice immediately after sacrifice. The tissues were washed in cold physiological saline, blotted and weighed. For ex vivo lipogenic assays, the portions of adipose tissues without blood vessels were used.

Assay for lipogenic activity

The rate of the incorporation of exogenous [$^{14}$C]-glucose into total lipid in adipose tissue was measured as the index of lipogenic activity[25,31,32]. Adipose tissues were sliced into segments of approximately 200 mg each and then placed in Krebs-Ringer Bicarbonate (KRB) buffer (pH 7.4) containing 1% defatted BSA and 1 mM glucose and gassed with 95% $O_2$–5% $CO_2$ at 37° C. After 1 hr preincubation, the tissues were transferred to another 2 ml of fresh media containing [$^{14}$C]-glucose (final specific activity 0.05 µCi/µmol) for a further 90 min incubation (conditions as above). Then the tissues were removed, washed thoroughly with KRB buffer and lipid was extracted with a chloroform/methanol mixture[33]. $^{14}$C radioactivity was counted in a Wallac 1410 Liquid Scintillation Counter. The rates of total lipid synthesis are expressed as pmol [$^{14}$C]-glucose incorporated into lipid/mg tissue/min.

statistical analysis

The Student's t-test was used to analyse the results. All data are expressed as the mean±SEM. P values of <0.05 are accepted as statistically significant.

RESULTS

Figure 1B:
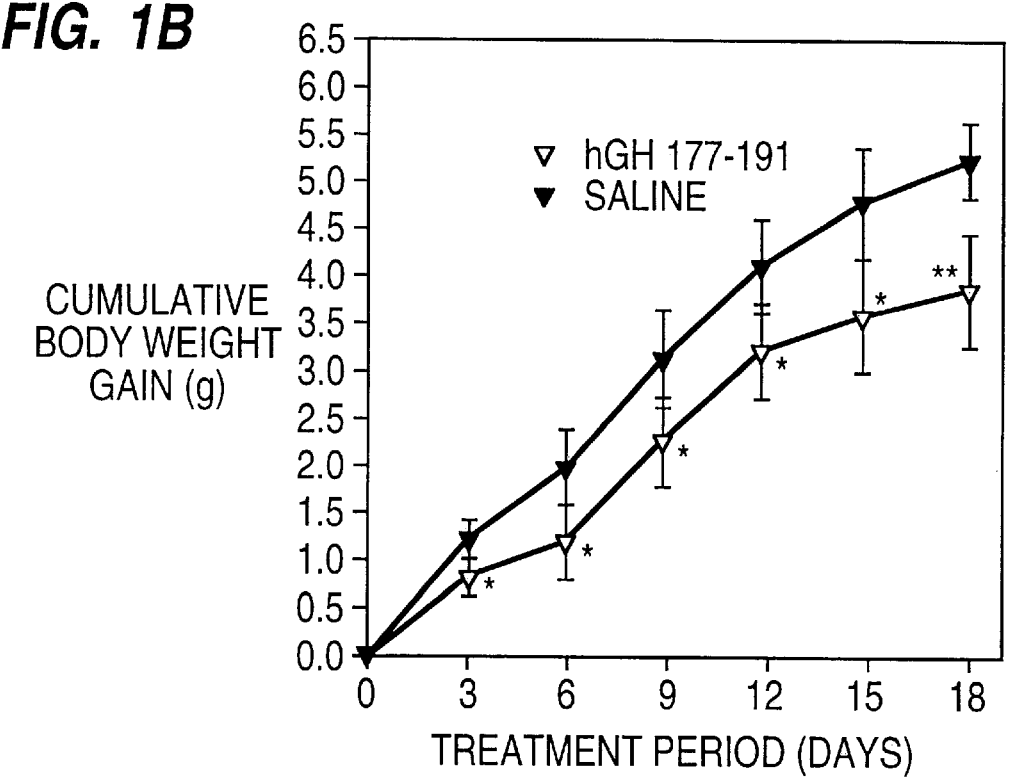
Figure 2:
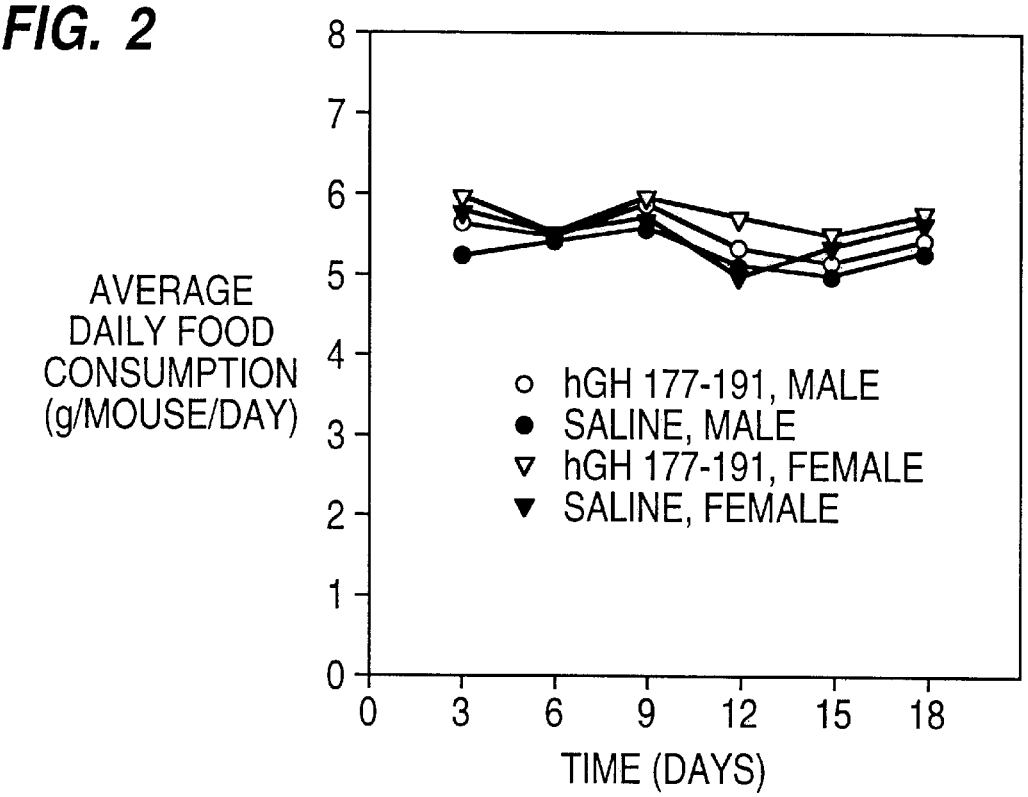
FIG. 2 shows the average daily food consumption (g/mouse/day) of C57BL/6J (ob/ob) mice during an 18-day treatment period with hGH 177–191 peptide. The treatment for the four groups of animals was as described in FIG. 1. Food consumption of each group was determined at 3-day intervals and each point represents the mean±SEM of 6 animals. No significance between the groups was observed at all times.

The chronic treatment of the obese mice with the synthetic hGH 177–191 peptide was evaluated by the measurements of a number of parameters including cumulative body weight gain and daily food consumption. FIG. 1 reveals that the control female animals appeared to have a larger mean cumulative body weight gain than their control male counterparts, similar to the observation previously reported by Ingalls et al.[34]. During the 18-day treatment period, a clear reduction of cumulative body weight gain was observed in the hGH 177–191-treated male as well as female animals when compared with the appropriate controls, indicating that the hGH fragment reduces the body weight gain in the obese mouse model. When the data were analysed and expressed as daily body weight gains, the treated male animals reduced their body weight gain from 0.22±0.03 to 0.16±0.04 g/day and the female animals from 0.30±0.02 to 0.22±g/day. The average daily body weight gains of the both male and female treated animals showed approximately 27% lower than those of the appropriate control groups. However, no significant difference in the average daily food consumption among the 4 groups was observed over the study period (FIG. 2). It was noted that the ratio of daily food consumption to daily body weight gain between the treated animals and control ones was different: 25±4 to 36±8 for the male mice and 18±2 to 27±6 for the female mice. These data clearly demonstrate that the chronic treatment with the hGH 177–191 peptide reduced the body weight gains without affecting food consumption.

Figure 3:
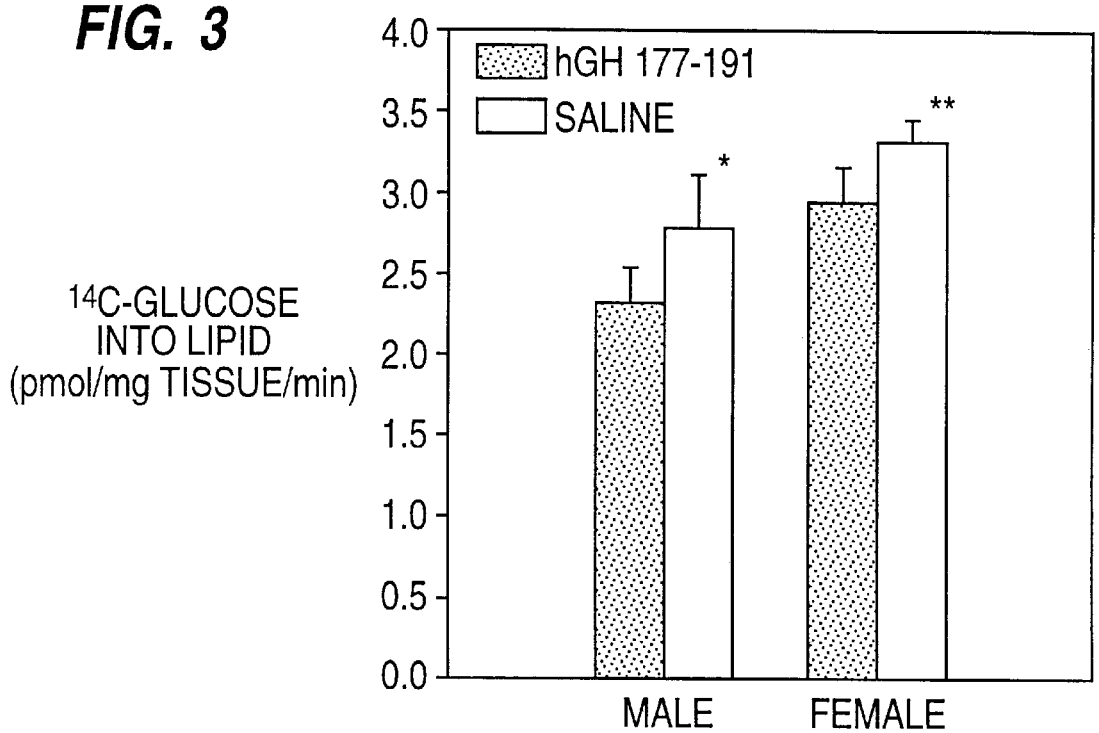
FIG. 3 shows the ex vivo effect on lipogenesis in adipose tissues of the C57BL/6J (ob/ob) mice after 18-day treatment with hGH 177–191. The tissues were preincubated at 37° C. for 1 hr in Krebs-Ringer Bicarbonate buffer (pH 7.4) containing 1% defatted BSA and 1 mM glucose. After preincubation, tissues were transferred to fresh media containing [$^{14}$C]-glucose (0.05 μCi/μmol) for a further 90 min incubation. Data indicate the rate of $^{14}$C-lipid synthesis and are expressed as $^{14}$C-glucose incorporated into lipid (pmol/mg tissue/min). Values are mean±SEM of 12 determinations from 6 animals of each group. The differences between the hGH 177–191 treated and saline control groups were statistically significant (*$p<0.1$, **$p<0.05$).

As indicated by the measurements of epididymal and parametrical fat pads, the treated mice significantly reduced their adipose tissue weights up to 20% in the males and 12% in the females as compared with the controls of the same sex (Table 1). Lipogenesis is subject to the supply of precursor metabolites such as glucose and acetate. The effect of hGH 177–191 on lipogenesis was therefore determined by measuring the incorporation of [$^{14}$C]-glucose into lipid in isolated adipose tissues. The hGH 177–191 peptide inhibited the lipogenesis from 2.80±0.33 to 2.33±0.21 pmol/mg tissue/min in the males and from 3.36±0.13 to 2.99±0.21 pmol/mg tissue/min in the females (FIG. 3). These results are consistent with the reductions in adipose tissue mass and cumulative body weight gain previously observed. Table 2 depicts the effect of the hGH 177–191 treatment on the profiles of circulating levels of triglyceride and cholesterol. The total cholesterol in plasma was significantly reduced from 4.44±0.56 to 3.52±0.39 mmol/l in the male animals, but the plasma levels of cholesterol in the treated female animals were only slightly lower than those of control ones. The responses to hGH 177–191 treatment between the male and female mice appeared to be different in this respect. On the other hand, hGH 177–191 did not influence the plasma levels of triglyceride in both sexes.

TABLE 1

Effect of synthetic hGH 177-191 peptide on body weight and adipose tissue mass of obese mice after 18-day chronic treatment. Animals were given a daily i.p. injection of either hGH 177-191 (200 μg/kg body weight) or equivalent volume of saline as control. All data represent the mean ± SEM of 6 animals (*p < 0.1; **p < 0.05).

| Item | Male | | Female | |
|---|---|---|---|---|
| | Control | Treated | Control | Treated |
| Initial body wt. (g) | 47.5 ± 3.1 | 48.6 ± 2.0 | 46.7 ± 3.6 | 48.2 ± 3.4 |
| Final body wt. (g) | 51.4 ± 3.0 | 51.5 ± 2.3 | 52.1 ± 3.2 | 52.2 ± 2.9 |
| Body wt. gain (g)[a] | 3.9 ± 0.6 | 2.9 ± 0.6* | 5.4 ± 0.4 | 4.0 ± 0.6** |
| Adipose tissue (g)[b] | 3.18 ± 0.43 | 2.52 ± 0.25** | 3.67 ± 0.54 | 3.26 ± 0.25** |

[a]The difference between the initial and final body weights were considered as body weight gain.
[b]The intact epididymal or parametrical fat pads were the representative adipose tissues.

TABLE 2

Effect of synthetic hGH 177-191 on plasma levels of triglyceride and total cholesterol in obese mice after 18-day chronic treatment. Blood samples were collected from the cut tips of the tails of the anaesthetised animals. Data represent the mean ± SEM of 6 animals (*p < 0.05).

| Item | Male | | Female | |
|---|---|---|---|---|
| | Control | Treated | Control | Treated |
| Triglyceride (mmol/l) | 0.63 ± 0.26 | 0.58 ± 0.16 | 0.41 ± 0.19 | 0.38 ± 0.11 |
| Cholesterol (mmol/l) | 4.44 ± 0.56 | 3.52 ± 0.39* | 3.01 ± 0.52 | 2.84 ± 0.29 |

REFERENCES

1. Ultsch, M. H., Somers, W., Kossiakof, A. A. and DeVos, A. M. (1994), *J. Mol. Biol.* 236: 286–299.
2. Ng, F. M., Bornstein, J., Welker, C., Zimmet, P. Z. and Taft, P. (1974). *Diabetes* 23: 943–949.
3. Frigeri, L. G., Teguh, C., Lind. N., Wolff, G. L. and Lewis, U. J. (1988). *Endocrinology* 122: 2940–2945.
4. Moore, W. V., Moore, K. C., McLachlan, C. G., Fuller, N. J., Burnett, G. B. and Frane, J. W. (1988). *Endocrinology* 122: 2920–2926.
5. Zeisel, H. J., Petrykowski, W. V. and Wais, U. (1992). *Horm. Res.* 37 (Suppl.2): 5–13.
6. Wabitsch, M. and Heinze, E. (1993). *Horm. Res.* 49: 5–9.
7. Christman, G. M. and Halme, J. K. (1992) *Fertil. Steril.* 57: 12–14.
8. Jacobs, H. S. (1992) *Horm. Res.* 38 (Suppl.1): 14–21.
9. Crist, D. M., Peake, G. T., Loftfield, R. B., Kraner, J. C. and Egan, P. A. (1991) *Mech. Ageing Dev.* 58: 191–205.
10. Strobl, J. S. and Thomas, M. J. (1994) *Pharm. Rev.* 46: 1–34.
11. Raben, M. S. and Hollenberg, C. H. (1959) *J. Clin. Invest.* 38: 484–488.
12. Bengtsson, B. A., Eden, S., Lonn, L., Kvist, H., Stokland, A., Lindstedt, G., Bosaeus, I., Tolli, J., Sjostorm, L. and Isaksson, O. G. P. (1993) *J. Clin. Endocrinol. Metab.* 76: 309–317.
13. Skaggs, S. R. and Crist, D. M. (1991) *Horm. Res.* 35: 19–24.
14. Etherton, T. D., Wiggins, J. P., Evock, C. M., Chung, C. S., Rebhun, J. F., Walton, P. E. and Steele, N. C. (1987). *J. Anim. Sci.* 64: 433–443.
15. Jiang, W. J., Shih, I. L., Tsai, H., Huang, Y. T. and Koh, T. J. (1993). 13th American Peptide Symposium, Edmonton, Canada, P-334 (Abstract).
16. Gertner, J. M. (1993) *Horm. Res.* 40: 10–15.
17. Davidson, M. B. (1987) *Endocrine Rev.* 8: 115–131.
18. Tai, P. K., Liao, J. F., Chen, E. H., Dietz, J., Schwards, J. and Carter-Su, C. (1990) *J. Biol. Chem.* 265: 21828–21834.
19. Dobo, M. (1975) PhD. Thesis, Department of Biochemistry, Monash University, Australia.
20. McNeillie, E. M. and Zammit, V. A. (1982) *Biochem. J.* 204: 273–288.
21. Gertner, J. M. (1992) *Horm. Res.* 38 (Suppl.2): 41–43.
22. Ng, F. M., Adamafio, N. A. and Graystone, J. E. (1990) *J. Mol. Endocrinol.* 4: 43–49.
23. Ng, F. M. and Heng, D. (1988) *Asia Pacific Commun. Biochem.* 2: 47–51.
24. Wu, Z. and Ng, F. M. (1993) *Biochem. Mol. Biol. Int.* 30: 187–96.
25. Wijaya, E. and Ng, F. M. (1993) *Biochem. Mol. Biol. Int.* 31: 543–552.
26. Applied Biosystems, Inc. (1989). Peptide Synthesizer User Bulletin 29, Applied Biosystems, Inc., Foster City, Calif., U.S.A.
27. King, D. S., Fields, C. G. and Fields, G. B. (1990) *Int. J. Peptide Protein Res.* 36: 255–266.
28. Akaji, K. A., Tatsumi, T., Yoshida, M., Kimura, T., Fujiwara, Y. and Kiso, Y. (1992) *J. Am. Chem. Soc.* 114:4137–4143.
29. Fossati, P., Prencipe, L. (1982) *Clin. Chem.* 28: 2077–80.
30. Allain, C. C., Poon, L. S., Chan, C. S. G., Richmond, W. and Fu, P. C. (1974) *Clin. Chem.* 20: 470–475.
31. Salem, M. A. M. and Wolff, G. L. (1989) *Proc. Soc. Exp. Biol. Med.* 191: 113–123.
32. Harris, D. M., Dunshea, F. R., Bauman, D. E., Boyd, R. D., Wang, S. Y., Johnson, P. A. and Clarke, S. D. (1993) *J. Anim. Sci.* 71: 3293–3300.
33. Folch, J., Lees, M. and Sloane-Stanley, G. H. (1957) *J. Biol. Chem.* 226: 397–503.
34. Ingalls, A. M., Dickie, M. M. and Snell, G. D. (1950) *J. Hered.* 41: 317–318.

We claim:

1. A method of treating obesity in an animal, comprising administering to an animal in need thereof an effective amount of a peptide, wherein the amino acid sequence of said peptide consists essentially of amino acid residues 177–191 of human growth hormone (hGH) (SEQ ID NO: 1), and wherein said peptide is not the intact, full-length human growth hormone.

2. The method according to claim 1, wherein the animal is a human.

3. The method according to claim 1, wherein the amino acid sequence of said peptide consists of amino acid residues 177–191 of hGH (SEQ ID NO: 1).

4. The method according to claim 1, wherein the amino acid sequence of said peptide consists of amino acid residues 172–191 of hGH (SEQ ID NO: 1).

5. The method according to claim 1, wherein the peptide is administered orally.

* * * * *

UNITED STATES PATENT AND TRADEMARK OFFICE
CERTIFICATE OF CORRECTION

PATENT NO. : 5,869,452
DATED : Febuary 9, 1999
INVENTOR(S) : Frrank Man-Woon NG et al.

It is certified that error appears in the above-identified patent and that said Letters Patent is hereby corrected as shown below:

On the cover page,
[73], Assignee, delete "MONASH UNIVERSITY" and replace with
--METABOLIC PHARMACEUTICALS LTD.--

Signed and Sealed this

Twenty-seventh Day of February, 2001

Attest:

NICHOLAS P. GODICI

Attesting Officer

Acting Director of the United States Patent and Trademark Office

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( x i ) SEQUENCE DESCRIPTION: SEQ ID NO:1:

```
Leu  Arg  Ile  Val  Gln  Cys  Arg  Ser  Val  Glu  Gly  Ser  Cys  Gly  Phe
1                   5                        10                       15
```

( 2 ) INFORMATION FOR SEQ ID NO:2:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( x i ) SEQUENCE DESCRIPTION: SEQ ID NO:2:

```
Lys  Val  Glu  Thr  Phe  Leu  Arg  Ile  Val  Gln  Cys  Arg  Ser  Val  Glu  Gly
1                   5                        10                       15

Ser  Cys  Gly  Phe
                20
```